(12) United States Patent
Tomlinson et al.

(10) Patent No.: US 8,288,464 B2
(45) Date of Patent: Oct. 16, 2012

(54) LOW-VOC POLYAMINES

(75) Inventors: Ian A. Tomlinson, Midland, MI (US); Asghar A. Peera, Cary, IL (US); Glenn Nelson Robinson, Naperville, IL (US)

(73) Assignees: Dow Global Technologies LLC, Midland, MI (US); ANGUS Chemical Company, Buffalo Grove, IL (US)

( * ) Notice: Subject to any disclaimer, the term of this patent is extended or adjusted under 35 U.S.C. 154(b) by 0 days.

(21) Appl. No.: 13/323,920

(22) Filed: Dec. 13, 2011

(65) Prior Publication Data

US 2012/0165463 A1    Jun. 28, 2012

Related U.S. Application Data

(60) Provisional application No. 61/427,273, filed on Dec. 27, 2010.

(51) Int. Cl.
*C08K 5/17* (2006.01)
*C07C 209/32* (2006.01)

(52) U.S. Cl. ...... 524/249; 564/478; 564/506; 106/287.3

(58) Field of Classification Search .......... 564/478, 564/506; 524/249; 106/287.3
See application file for complete search history.

(56) References Cited

U.S. PATENT DOCUMENTS

| | | | | |
|---|---|---|---|---|
| 2,046,720 | A | * | 7/1936 | Bottoms ............ 564/478 |
| 2010/0275816 | A1 | | 11/2010 | Swedo |
| 2010/0326320 | A1 | * | 12/2010 | Swedo et al. ........ 106/18.32 |
| 2012/0035298 | A1 | | 2/2012 | Tomlinson et al. |

OTHER PUBLICATIONS

Duffy, et al., "Reaction Kinetics for Hindered Amine/Epoxides by DSC," J. Applied Polymer Sciences, vol. 33, pp. 2959-2964 (1987).
Butler, "Studies in the Mechanism of the Mannich Reaction. I. The Reaction of Methylenediamines with 2-Methyl-2-nitro-1-propanol," J. Am. Chem. Soc., vol. 78, pp. 482-484 (1956).

* cited by examiner

*Primary Examiner* — Ling-Siu Choi
*Assistant Examiner* — John Uselding
(74) *Attorney, Agent, or Firm* — Kenneth Crimaldi

(57) ABSTRACT

A compound having formula (I)

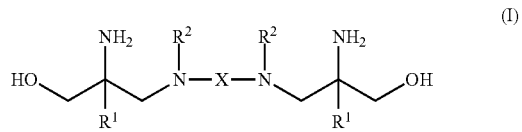

(I)

wherein $R^1$ is methyl or ethyl; $R^2$ is hydrogen, methyl, $CH_2C(NH_2)(R^1)(CH_2OH)$ or $R^2$ groups combine to form a difunctional $C_2$-$C_6$ alkyl group; and X is a difunctional group selected from the group consisting of $C_2$-$C_{20}$ alkyl, $C_5$-$C_{20}$ cycloalkyl, $C_6$-$C_{10}$ aryl, $C_8$-$C_{20}$ aryl alkyl, $C_4$-$C_{20}$ heteroalkyl or $C_{10}$-$C_{20}$ aryl heteroalkyl.

6 Claims, No Drawings

LOW-VOC POLYAMINES

BACKGROUND

This invention relates generally to a polyamine compound useful in coating compositions and other applications for pH adjustment.

G. B. Butler, *J. Am. Chem. Soc.*, 1956, 78, 482-484, discloses a compound having the formula

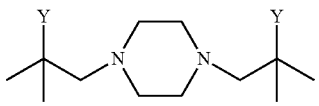

where Y=$NO_2$, $NH_2$, but this reference does not disclose or suggest a hydroxy-substituted polyamine or nitro-amine compound as claimed in the present application.

The problem addressed by this invention is to find new polyamine compounds useful in coating compositions and other applications for pH adjustment.

STATEMENT OF INVENTION

The present invention is directed to a compound having formula (I)

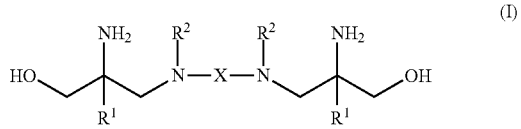

wherein $R^1$ is methyl or ethyl; $R^2$ is hydrogen, methyl, $CH_2C(NH_2)(R^1)(CH_2OH)$ or $R^2$ groups combine to form a difunctional $C_2$-$C_6$ alkyl group; and X is a difunctional group selected from the group consisting of $C_2$-$C_{20}$ alkyl, $C_5$-$C_{20}$ cycloalkyl, $C_6$-$C_{10}$ aryl, $C_8$-$C_{20}$ aryl alkyl, $C_4$-$C_{20}$ heteroalkyl or $C_{10}$-$C_{20}$ aryl heteroalkyl.

The present invention is further directed to a compound having formula (II)

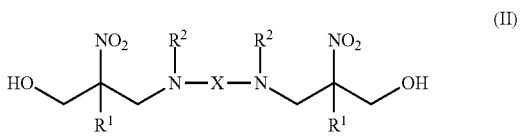

wherein $R^1$ is methyl or ethyl; $R^2$ is hydrogen, methyl, $CH_2C(NO_2)(R^1)(CH_2OH)$ or $R^2$ groups combine to form a difunctional $C_2$-$C_6$ alkyl group; and X is a difunctional group selected from the group consisting of $C_2$-$C_{20}$ alkyl, $C_5$-$C_{20}$ cycloalkyl, $C_6$-$C_{10}$ aryl, $C_8$-$C_{20}$ aryl alkyl, $C_4$-$C_{20}$ heteroalkyl or $C_{10}$-$C_{20}$ aryl heteroalkyl.

The present invention is further directed to a method for adjusting pH in a coating composition; said method comprising adding to a coating composition having a pH below 7 a sufficient amount of a compound of formula (I) to produce a final pH from 7.5 to 9.5 wherein $R^1$ is methyl or ethyl; $R^2$ is hydrogen, methyl, $CH_2C(NO_2)(R^1)(CH_2OH)$ or $R^2$ groups combine to form a difunctional $C_2$-$C_6$ alkyl group; and X is a difunctional group selected from the group consisting of $C_2$-$C_{20}$ alkyl, $C_5$-$C_{20}$ cycloalkyl, $C_6$-$C_{10}$ aryl, $C_8$-$C_{20}$ aryl alkyl, $C_4$-$C_{20}$ heteroalkyl or $C_{10}$-$C_{20}$ aryl heteroalkyl.

DETAILED DESCRIPTION

All percentages are weight percentages ("wt %"), unless otherwise indicated. Concentrations in parts per million ("ppm") are calculated on a weight/volume basis. An "aqueous" composition is one comprising at least 30 wt % water, alternatively at least 35 wt % water, alternatively at least 38 wt % water. Preferably, aqueous compositions comprise no more than 5 wt % organic solvent. An "alkyl" group is a hydrocarbyl group having from one to twenty carbon atoms, unless otherwise specified, in a linear or branched arrangement. Alkyl groups optionally have one or more double or triple bonds. Substitution on alkyl groups of one or more hydroxy or alkoxy groups is permitted. Preferably, alkyl groups are saturated and unsubstituted. A "cycloalkyl" group is an alkyl group containing at least one saturated ring. A "heteroalkyl" group is an alkyl group in which at least one carbon has been replaced by O, NR, or S, wherein R is hydrogen, alkyl, aryl or aralkyl; e.g., —$CH_2CHR'(OCH_2CHR')_n$— where R' is hydrogen, methyl or ethyl and n is from one to nine, or an upper limit determined by the maximum size of the heteroalkyl group and the identity of R'. The carbon number of a heteroalkyl group is the actual number of carbon atoms in the heteroalkyl group, and does not include incorporated heteroatoms. In some embodiments of the invention, a heteroalkyl group has only oxygen heteroatoms and the ratio of carbon atoms to oxygen atoms is from 5:1 to 2:1, alternatively from 4:1 to 2.5:1. In some embodiments of the invention, a heteroalkyl group has only nitrogen heteroatoms and the ratio of carbon atoms to nitrogen atoms is at least 2:1. In some embodiments of the invention, a heteroalkyl group containing at least one nitrogen atom has a —$CH_2C(Y)(R^1)(CH_2OH)$ group bonded to a nitrogen atom, wherein Y is $NO_2$ or $NH_2$ in compound (II) or compound (I), respectively. In some embodiments of the invention, a heteroalkyl group is attached through carbon atoms at either end of the chain. An "aryl" group is a substituent derived from an aromatic hydrocarbon compound. An aryl group has a total of from six to twenty ring atoms, unless otherwise specified, and has one or more rings which are separate or fused. An "aralkyl" group is an "alkyl" group substituted by an "aryl" group. An "aryl alkyl" group is a difunctional group in which a difunctional aryl group is inserted into an alkyl group, e.g., —$(CH_2)_xC_6H_4(CH_2)_y$—, where $C_6H_4$ is o-, m- or p-phenylene and x and y may be the same or different, preferably the same, and have values consistent with the overall size of the aryl alkyl group and the identity of the inserted aryl group. An "aryl heteroalkyl" group is a difunctional group in which a difunctional aryl group is inserted into a heteroalkyl group. Substitution on aryl groups of one or more of the following groups: halo, cyano, nitro, hydroxy, alkoxy, alkyl, heteroalkyl, alkanoyl, amino, or amino substituted by one or more of alkyl, aryl, aralkyl, heteroalkyl or alkanoyl is permitted, with substitution by one or more halo groups being possible on alkyl, heteroalkyl, alkanoyl or alkoxy groups. Preferably, aryl groups do not contain halogen atoms. In one preferred embodiment of the invention, aryl groups are unsubstituted or substituted only by alkyl groups. A difunctional group is a substituent group having two points of attachment, e.g., one example of a difunctional alkyl group would be —$(CH_2)_x$—, where x could be from two to twenty.

In some embodiments of the invention, $R^2$ is $CH_2C(NO_2)(R^1)(CH_2OH)$ in compound (II) or $CH_2C(NH_2)(R^1)(CH_2OH)$ in compound (I). In some embodiments, the $R^2$ substituents combine to form a $C_2$ difunctional alkyl group, and preferably, X also is a $C_2$ difunctional alkyl group.

In some embodiments of the invention, X is a difunctional group selected from the group consisting of $C_2$-$C_{10}$ alkyl, $C_5$-$C_{10}$ cycloalkyl, $C_6$-$C_8$ aryl, $C_8$-$C_{12}$ aryl alkyl, $C_4$-$C_{10}$ heteroalkyl and $C_{10}$-$C_{16}$ aryl heteroalkyl; alternatively $C_2$-$C_{10}$ alkyl, $C_4$-$C_{10}$ heteroalkyl and $C_{10}$-$C_{16}$ aryl heteroalkyl; alternatively $C_3$-$C_8$ alkyl and $C_4$-$C_8$ heteroalkyl. In some embodiments of the invention, X is symmetric, i.e., there is a plane of symmetry perpendicular to the length of X.

In some embodiments of the invention, the compound of formula (I) is prepared by combining a nitro diol of formula (III) with a compound having two terminal amino groups, as in formula (IV), with $R^1$, $R^2$ and X as defined above, and $R^3$ is hydrogen or methyl, as shown below

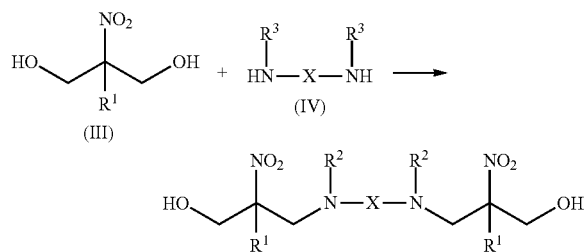

to produce a nitro compound of formula (II), followed by reduction of nitro compound (II) to the compound of formula (I). Reduction of compound (II) may be accomplished using any reagent capable of reducing aliphatic nitro groups. Examples of such reducing agents include hydrogen gas in combination with a catalyst, for example, Raney nickel, a platinum or palladium containing catalyst, e.g., Pt or Pd in elemental form or their oxides, with or without inorganic supports, e.g., carbon; and other reducing agents including metal/acid combinations, e.g., iron/acetic acid, aluminum hydrides, e.g., lithium aluminum hydride or sodium bis(2-methoxyethoxy)aluminum hydride. Preferred reducing agents include hydrogen gas in combination with any of the following catalysts: Raney nickel, platinum or palladium. Conditions for hydrogenation of nitro groups are well known, e.g., a temperature range of about 20-80° C. at a pressure of about 100-1000 psi (690-6900 kPa), and can be adjusted easily by one skilled in the art.

In some embodiments of the invention, compound (IV) has polymerized residues, e.g., two-six residues, of alkylene oxides, e.g., ethylene oxide, propylene oxide and butylene oxide, capped with aminoalkyl groups, e.g., $C_2$-$C_4$ aminoalkyl groups. In some embodiments of the invention, X represents a mixture of groups having the average formula —$CH(CH_3)CH_2(OCH_2CH(CH_3))_n$—, where n is about 2.7. This mixture contains at least the species having n equal to 2, 3 and 4, which correspond to X being a $C_9$, $C_{12}$ or $C_{15}$ heteroalkyl group, respectively.

In some embodiments of the invention, a molar ratio of compound (III) to compound (IV) is approximately two, resulting in one mole of compound (III) becoming attached to each end of compound (IV), so that $R^2$ in the product is hydrogen or methyl. Of course in cases where $R^3$ in compound (IV) is methyl, $R^2$ will be methyl. However, if $R^3$ is hydrogen and the ratio of compound (III) to compound (IV) is more than two, then compounds in which $R^2$ is $CH_2C(NO_2)(R^1)(CH_2OH)$ will be formed. In some embodiments of the invention, X is a heteroalkyl group containing at least one nitrogen atom which has a hydrogen atom. In these cases, if the ratio of compound (III) to compound (IV) is greater than two, then compounds having a $CH_2C(NO_2)(R^1)(CH_2OH)$ group attached to the heteroalkyl nitrogen atom are formed. For example, if X is $CH_2CH_2NHCH_2CH_2$ and the ratio of compound (III) to compound (IV) is approximately five, the following compound is formed

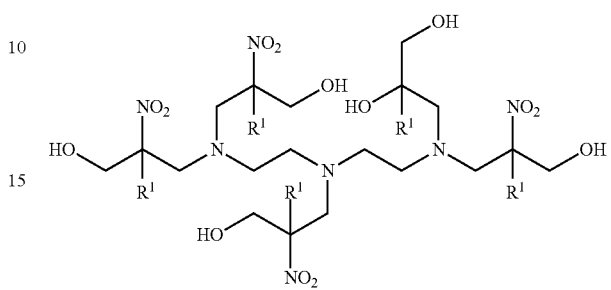

When the compound of formula (I) is used to adjust pH in an aqueous coating composition or other aqueous composition having an initial pH less than 7, the amount of compound (I) added clearly can vary depending on the initial pH, desired final pH, and other components present in the composition. However, one skilled in the art can easily determine the necessary amount of compound (I). In acrylic latex coating compositions, typically the amount of compound (I) would be in the range from 10 wt % to 125 wt % of total weight of carboxylic acid groups in the coating composition, alternatively from 25 wt % to 100 wt %. In some embodiments of the invention, the initial pH of the aqueous composition is from 2-7, alternatively from 2.5-6. The target pH value preferably is from 7.8 to 9.3, alternatively from 8 to 9.2. In some embodiments of the invention, the aqueous coating composition is an acrylic latex comprising copolymers of acrylic or methacrylic acid with $C_1$-$C_8$ alkyl acrylates or methacrylates. In some embodiments of the invention, the acrylic latex comprises 40-65 wt % polymer solids, alternatively 45-62 wt %, alternatively 45-55 wt %.

Conditions for reaction of compounds (III) and (IV) are generally known, e.g., typically the reactants are heated to reflux for 1-10 hours and then optionally kept at room temperature (20-25° C.) for up to 24-48 hours. There are many suitable solvents, e.g., water, methanol, ethanol, and mixtures thereof.

EXAMPLES

Preparation of 2-methyl-2-nitropropane-1,3-diol

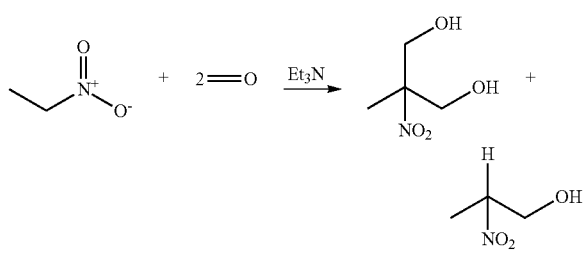

A 3 neck round bottom flask equipped with stir bar and condenser capped with a nitrogen outlet and dropping funnel was charged with nitroethane (10 g, 0.13 mol) and triethylamine (0.3 g, 10 mol %). The pale yellow solution was stirred for 10 min and 37% solution of formaldehyde (21.6 g, 0.27 mol) was added drop wise over a period of 1 h. The reaction was stirred at room temperature for 24 h and the reaction monitored periodically by GC to check the disappearance of the starting materials. The reaction was stopped after 24 h and the volatiles removed by rotary evaporator. The resulting solution was yellow in color and GC analysis the presence of two products. The product mixture was used in the subsequent reactions without further purification.

| Product | Ret. Time (min) | Yield, (%) | m/z |
|---|---|---|---|
| 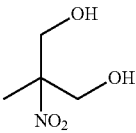 | 11.66 | 70 | 105 |
| 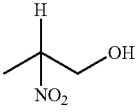 | 7.30 | 30 | 75 |

Preparation of Piperazine Adduct (7)

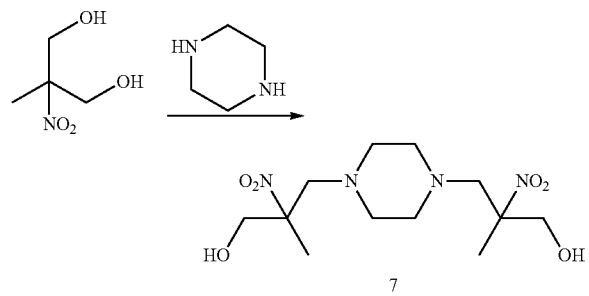

To a stirred solution of piperazine (5.7 g, 0.07 mol) in 15 mL methanol was added drop wise a mixture of 2-methyl-2-nitropropane-1,3-diol and 2-nitropropan-1-ol (17.96 g). The reaction mixture was stirred for 30 minutes at room temperature followed by refluxing for 5 h. During the reaction, a white precipitate was formed which was barely soluble in water and in methanol. The white solid was filtered and dried under vacuo for 2 h. The yield after drying in vacuo was 20 g (90%) of the desired compound.

$^1$H NMR (DMSO-$d_6$): ∂ 1.46 (s, 6H), ∂ 2.50 (s, 2H), ∂ 3.17 (s, 8H), ∂ 3.7 (s, 4H) and ∂ 5.31 (d, 4H). $^{13}$C NMR (DMSO-$d_6$): ∂ 16.8, 48.5, 54.5, 63.9 and 93.0 ppm.

Preparation of NEPD-HMDA Analogue (9)

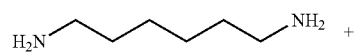

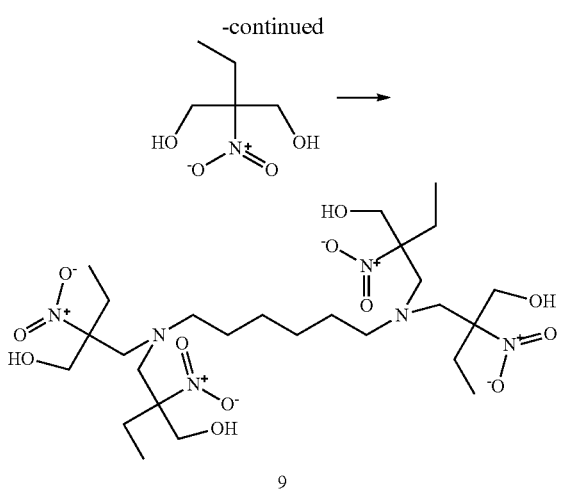

To a 1 neck round bottom flask equipped with stir bar and dropping funnel capped with a nitrogen outlet was added hexamethylenediamine (HMDA) (20 g, 0.17 mol). A 55% aqueous solution of the mixture of 2-nitro-2-ethyl-1,3-propanediol and 2-ethyl-2-nitrobutanol (189 g, 0.69 mol) was added drop wise to the flask over a period of 1 h with continuous stirring. After complete addition, the dropping funnel was replaced by a condenser and the reaction mixture refluxed for 6 h and stirred at room temperature overnight. After completion of the reaction, the content of the flask was filtered through suction filtration and the deep red high viscous material was collected and dried under vacuum for 8 h. The molecule was too bulky to be detected in GC/MS. The sample was passed through the HPLC Column (90/10 water/acetonitrile) and it showed the formation of three different products. The HPLC retention times recorded were 1.27, 1.66 and 1.91 minutes, with the most polar compound i.e., retention time 1.27 min was formed in greatest amount.

Preparation of NEPD-DETA Analogue (10)

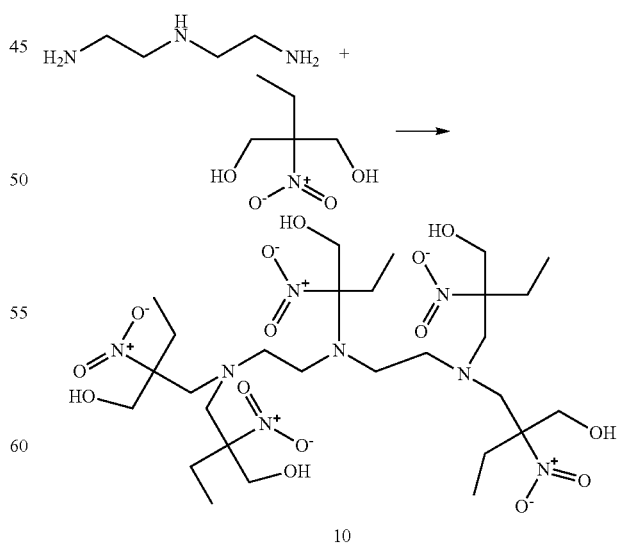

To a 1 neck round bottom flask equipped with stir bar and dropping funnel capped with a nitrogen outlet was added diethylenetriamine (DETA) (10 g, 0.09 mol). A 55% aqueous solution of the mixture of 2-nitro-2-ethyl-1,3-propanediol and 2-ethyl-2-nitrobutanol (132 g, 0.48 mol) was added drop wise to the flask over a period of 1 h with continuous stirring. After complete addition, the dropping funnel was replaced by a condenser and the reaction mixture refluxed for 6 h and stirred at room temperature overnight. After completion of the reaction, the content of the flask was filtered through suction filtration and the deep red high viscous material was collected and dried under vacuum for 8 h. The molecule was too bulky to be detected in GC/MS. The sample was passed through the HPLC Column (90/10 water/acetonitrile) and it showed the formation of two different products. The HPLC retention times recorded were 1.27 and 1.92 minutes, with the most polar compound i.e., retention time 1.27 min was formed in greatest amount.

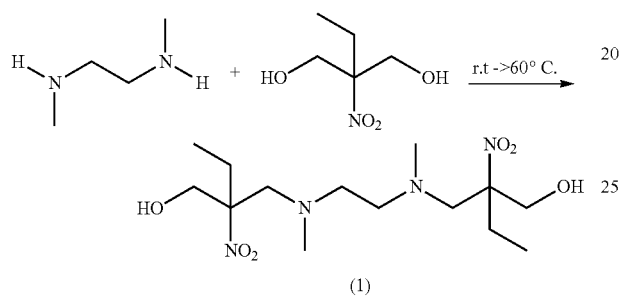

A 100 mL 3-neck flask equipped with a magnetic stirrer, nitrogen blanket, thermocouple, condenser and addition funnel is charged with N,N'-dimethylethane-1,2-diamine (7.0 g/0.08 moles, 1.0 equivalents). The addition funnel charged with 2-ethyl-2-nitropropane-1,3-diol (69.2 wt % NEPD in water: 34.4. g/0.15 moles, 2.01 equivalent). The NEPD was added very slowly to the amine in the flask, over a period of 15-20 minutes. A slight exotherm of 10-12° C. was observed and the reaction mixture turned yellow. The mixture was heated to 60° C. for 10 h, followed by room temperature stir for additional 17 h. During heating, the reaction mixture turned deep red. At this point, the reaction was deemed complete and was stopped. The total amount of material plus water was approximately 50 g. LC-MS analysis confirmed the formation of Compound (1) as the major product, [M+H]=351.22. There was a minor impurity with [M+H]=337.21. The reaction product was used as-is in the hydrogenation reaction step.

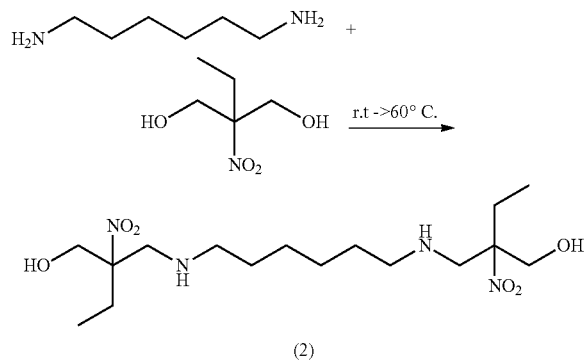

A 100 mL 1-neck flask equipped with a magnetic stirrer, nitrogen blanket and addition funnel is charged with hexane-1,6-diamine (10.0 g/0.09 moles, 1.0 equivalents). The addition funnel charged with 2-ethyl-2-nitropropane-1,3-diol (69.2 wt % NEPD in water: 37 g/0.17 moles, 2.01 equivalent). The NEPD was added very slowly to the amine in the flask, over a period of 15-20 minutes. The reaction mixture became warm upon mixing the NEPD and turned cloudy and yellow in color. The addition funnel was replaced by a condenser and the reaction mixture heated to 60° C. for 10 h, followed by room temperature stir for additional 24 h. Stirring the reaction mixture overnight, resulted in two layers i.e., the aqueous layer and a gel like layer, yellow in color. At this point, the reaction was deemed complete. The aqueous layer was decanted and ~25.8 g (79.4%) of gel like yellow material obtained. LC-MS analysis confirmed the formation of Compound (2) as the only product, [M+H]=379.24. The reaction product was used as-is in the hydrogenation reaction step

The invention claimed is:

1. A compound having formula (I)

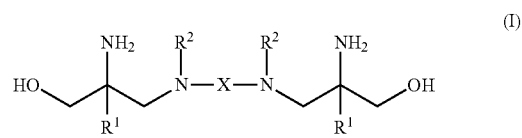

wherein $R^1$ is methyl or ethyl; $R^2$ is hydrogen, methyl, $CH_2C(NH_2)(R^1)(CH_2OH)$ or $R^2$ groups combine to form a difunctional $C_2$-$C_6$ alkyl group; and X is a difunctional group selected from the group consisting of $C_2$-$C_{20}$ alkyl, $C_5$-$C_{20}$ cycloalkyl, $C_6$-$C_{10}$ aryl, $C_8$-$C_{20}$ aryl alkyl, $C_4$-$C_{20}$ heteroalkyl or $C_{10}$-$C_{20}$ aryl heteroalkyl.

2. The compound of claim 1 in which X is $C_3$-$C_8$ alkyl or $C_4$-$C_8$ heteroalkyl.

3. The compound of claim 2 in which $R^2$ is $CH_2C(NH_2)(R^1)(CH_2OH)$.

4. The compound of claim 3 in which X is a $C_4$-$C_8$ heteroalkyl group having at least one nitrogen atom, and a $CH_2C(NH_2)(R^1)(CH_2OH)$ group is attached to a heteroalkyl nitrogen atom.

5. A method for adjusting pH in a coating composition; said method comprising adding to a coating composition having a pH below 7 a sufficient amount of a compound of formula (I)

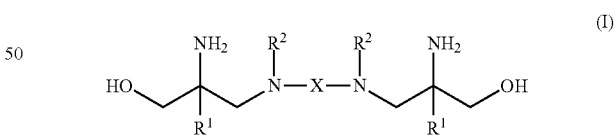

wherein $R^1$ is methyl or ethyl; $R^2$ is hydrogen, methyl, $CH_2C(NH_2)(R^1)(CH_2OH)$ or $R^2$ groups combine to form a difunctional $C_2$-$C_6$ alkyl group; and X is a difunctional group selected from the group consisting of $C_2$-$C_{20}$ alkyl, $C_5$-$C_{20}$ cycloalkyl, $C_6$-$C_{10}$ aryl, $C_8$-$C_{20}$ aryl alkyl, $C_4$-$C_{20}$ heteroalkyl or $C_{10}$-$C_{20}$ aryl heteroalkyl;
to produce a final pH from 7.5 to 9.5.

6. The method of claim 5 in which X is $C_3$-$C_8$ alkyl or $C_4$-$C_8$ heteroalkyl.

* * * * *